United States Patent [19]

Barth

[11] Patent Number: 5,685,834
[45] Date of Patent: Nov. 11, 1997

[54] SURGICAL DRESSING MATERIAL

[76] Inventor: Alan H. Barth, 6141 Cypress Point Rd., San Diego, Calif. 92120

[21] Appl. No.: 282,806

[22] Filed: Jul. 29, 1994

[51] Int. Cl.$^6$ .................................................. A61L 15/00
[52] U.S. Cl. .................................. 602/75; 602/42
[58] Field of Search ........................... 602/42, 43, 44, 602/45, 46, 48, 53, 903, 75; 604/304, 358, 367

[56] References Cited

U.S. PATENT DOCUMENTS

| | | | |
|---|---|---|---|
| 3,670,731 | 6/1972 | Harmon | 602/42 |
| 3,678,933 | 7/1972 | Moore et al. | 602/42 |
| 4,005,709 | 2/1977 | Laerdal | 602/53 |
| 4,341,207 | 7/1982 | Steer et al. | 128/155 |
| 4,345,591 | 8/1982 | Hedgren | 602/53 |
| 4,445,604 | 5/1984 | Lang | 602/47 |
| 4,603,076 | 7/1986 | Bowditch et al. | 602/43 |
| 5,064,653 | 11/1991 | Sessions et al. | 424/445 |
| 5,065,752 | 11/1991 | Sessions et al. | 128/156 |
| 5,271,987 | 12/1993 | Iskra | 604/367 |
| 5,383,900 | 1/1995 | Krantz | 602/903 |
| 5,409,472 | 4/1995 | Rawlings | 604/307 |

*Primary Examiner*—Corrine M. McDermott
*Assistant Examiner*—Cris L. Rodriguez
*Attorney, Agent, or Firm*—Henri J. A. Charmasson; John D. Buchaca

[57] ABSTRACT

A surgical dressing comprises a slab or strip of open-cell synthetic foam material sandwiched between layers of gauze. The foam slab provides good absorption capacity and homogeneity to the dressing while reducing adherence to dried wounds. The foam slab also adds some rigidity to a strip of dressing which can then be used to form compressing and stabilizing bandages.

10 Claims, 2 Drawing Sheets

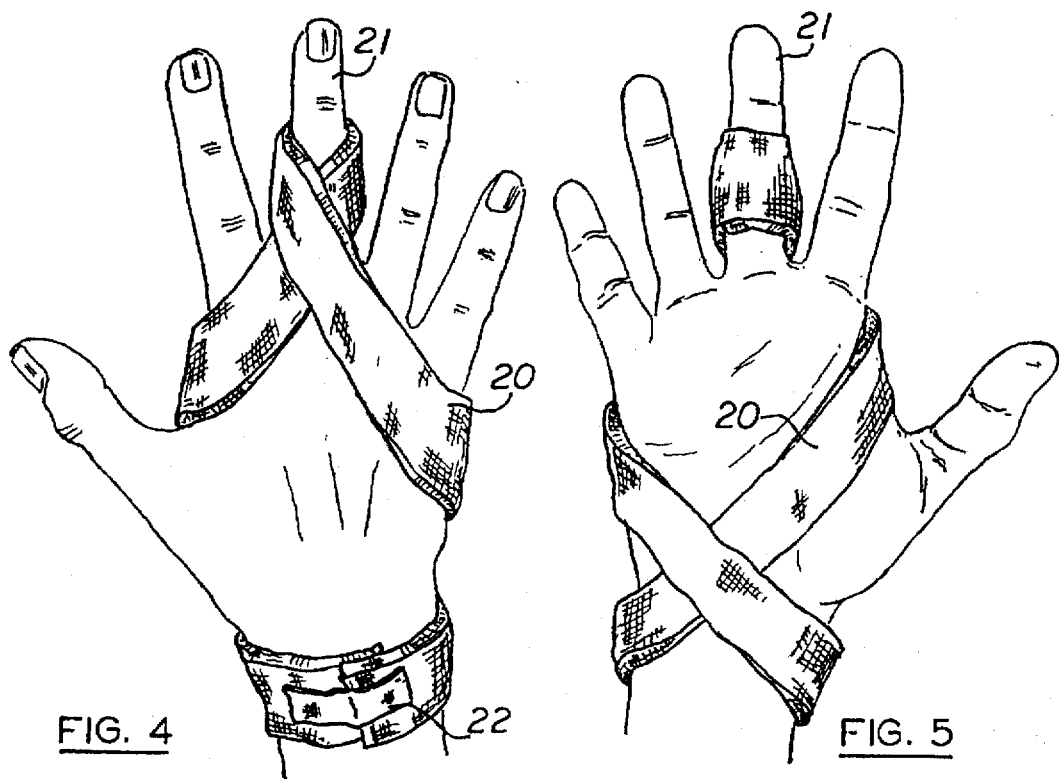
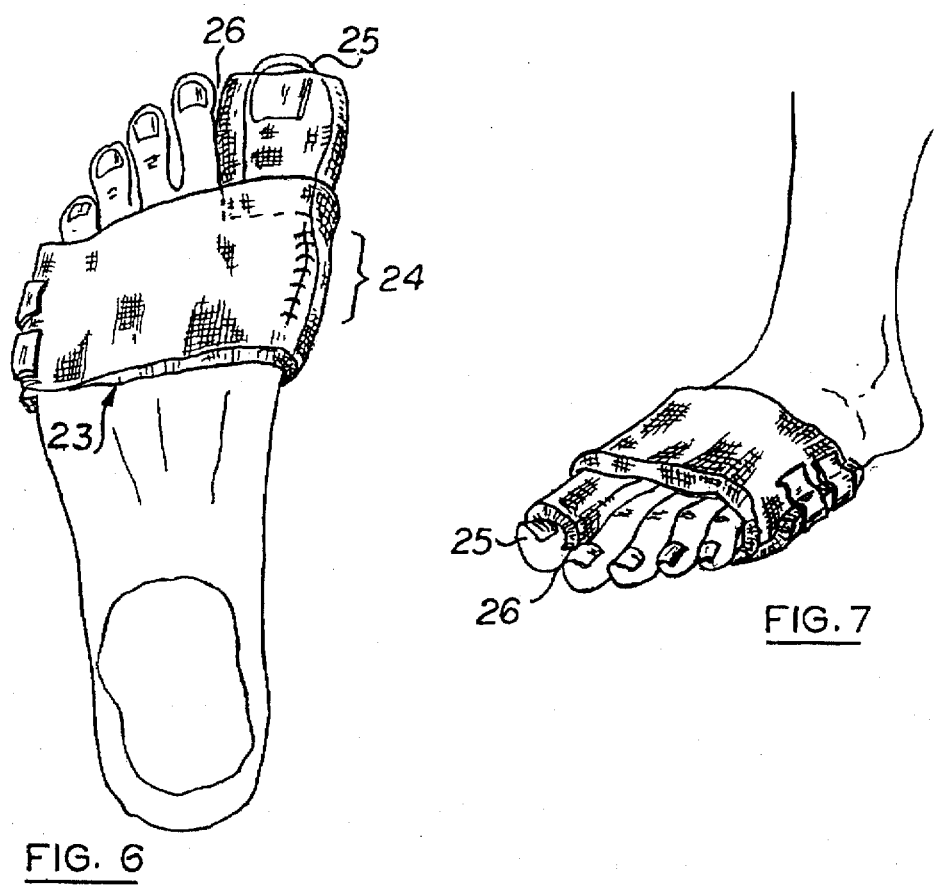

SURGICAL DRESSING MATERIAL

FIELD OF THE INVENTION

This invention relates to surgical as well as orthopedic dressings and bandages.

BACKGROUND OF THE INVENTION

Dressings and bandages are used in the treatment of wounded or broken body parts to (a) absorb blood and seal wounds, (b) hold therapeutic preparations against the injured tissues, (c) limit swelling by compression, (d) stabilize broken bones by support and motion restriction, (e) protect the ailing tissue against shocks, and (f) shield open wounds against contamination. Surgical and orthotic dressings are commonly fashioned from multi-layered sterile gauze pads and compresses covered by bandages, sometimes combined with splints. Small blocks, wedges or rods of sponge or other resilient materials are also used in combination with pads, bandages and splints to support and immobilize fingers, toes, elbows, ankles and other joints.

These various elements must be carefully combined and bound together to achieve the desired therapy. Installation and removal are lengthy and often cumbersome procedures. Adherence of the gauze pads and compresses to dried blood render the removal of such dressings difficult for the therapist and often painful to the patient. Gauze pads and compresses have a limited capacity for holding therapeutic preparations.

SUMMARY OF THE INVENTION

The principal and secondary objects of the invention are to provide a new surgical and orthopedic sterile dressing medium that affords good absorption, resilient compression, support and protection, and can be quickly and conveniently put in place and removed while offering added capacity to hold disinfectant and other healing preparations against the damaged tissues.

These and other objects are achieved by pads and bandages made from open-cell synthetic foam slabs sandwiched between layers of gauze. The new dressing material can be supplied in the form of rolls from which strip sections of the composite dressing can be conveniently dispensed.

The new dressing material can be used in a variety of arrangements to form post-operative stabilizing bandages.

BRIEF DESCRIPTION OF THE DRAWINGS

FIG. 4 is a top plan view of a patient's hand dressed to protect and support a phalangeal trauma;

FIG. 5 is a bottom plan view thereof;

FIG. 6 is a top view of a patient's foot with a post-bunionectomy dressing; and

FIG. 7 is a perspective view thereof.

DESCRIPTION OF THE PREFERRED EMBODIMENTS OF THE INVENTION

Figure 1:
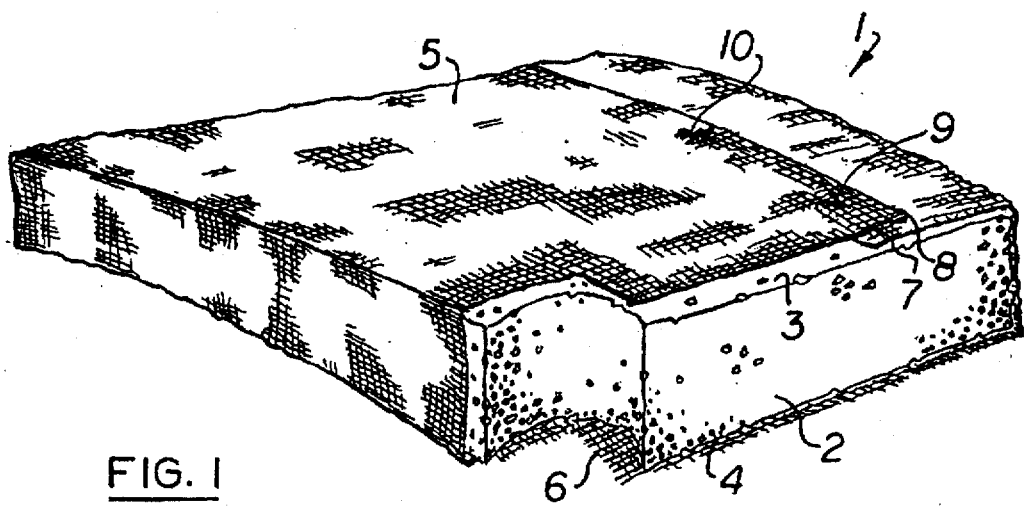
FIG. 1 is a perspective view of a section of dressing according to the invention.

Referring now to the drawing, there is shown in FIG. 1 a composite surgical dressing 1 according to the invention.

This dressing comprises a slab 2 of spongeous material, preferably an open-cell synthetic foam. The flat top surface 3 and flat bottom surface 4 are respectively covered by a top layer 5 and a bottom layer 6 of gauze. Preferably, a strip of gauze having the same length as the slab and a width at least double to it, is transversally wrapped around the slab and the overlapping edges 7 and 8 of the gauze strip are secured together and to the slab by a plurality of stitches 9, 10 at regular intervals along the length of the dressing.

Although the top and bottom layers and slab have similar length and width dimensions, due to manufacturing imprecision, bending of the slab during application, and the wrap-around nature of the gauze strip, the layers and slab are said to be substantially commensurate.

Figure 2:
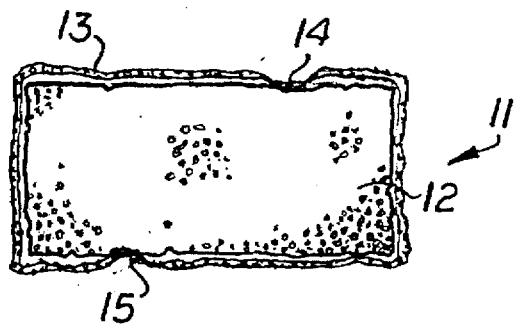
FIG. 2 is a cross-sectional view of an alternate embodiment thereof.
Figure 3:
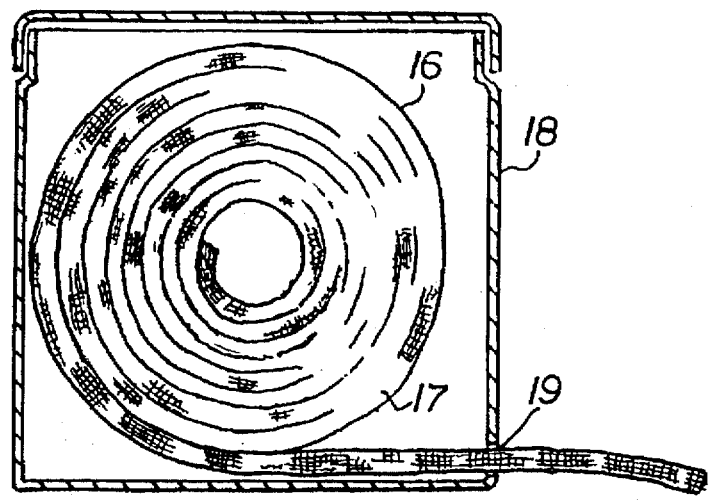
FIG. 3 is a cross-sectional view of a roll of such dressing in a dispensing container.

An alternate embodiment of the invention 11 is illustrated in FIG. 2. In this embodiment the spongeous slab 12 is surrounded by a strip of gauze 13 wrapped around it to form multiple layers. At least the first layer of gauze in contact with the top and bottom faces of the slab is partially embedded into the slab surfaces at various points 14, 15 along the length of the dressing. This type of bonding is achieved by applying a hot tip to the surface of the dressing which causes part of the spongeous material to melt around the fibers of the gauze.

Preferably, the dressing is manufactured in long strips 16 which are packaged into rolls 17 and placed within a dispensing container 18, a slot 19 in a wall of the container allows the pulling out of lengths of the roll which can be cut into bandages or pads as needed.

The thickness of the slab 2, 12 is preferably between 1 centimeter and 3 centimeters. Its width can vary from 3 centimeters to 20 centimeters depending upon the prescribed use.

At least one layer of gauze closest to the spongeous slab is preferably wrapped tightly around it in order to partially compress the slab and increase its rigidity. Strips of such dressing of a variety of sizes and rigidities can thus be manufactured and prescribed for a range of specific applications.

FIGS. 4 and 5 illustrate how a strip of dressing material 20 can be used to stabilize an injured middle finger 21. In this case, a strip of composite dressing according to the invention having a foam thickness of approximately 2 centimeters and a slab width of approximately 3 centimeters is used. The bottom of the finger 21 is placed against the middle section of the strip of dressing. The left and right halves of the strip are then crossed over the top of the finger 21 then wrapped around the hand, crossed over the palm and finally secured around the wrist by a strip of adhesive tape 22 or other convenient fastener.

FIGS. 6 and 7 illustrate the surgical dressing and immobilizing of a foot after a bunionectomy. After such a procedure the surgical site 24 (shown in transparency on the drawing) at the first metatarsal-phalangeal joint must be dressed, and the hallux 25 must be immobilized. In the prior art, such a procedure requires a combination of dressing compresses, bandages and splints. A strip of dressing 23 according to the invention having a slab width of approximately 5 centimeters and a thickness of approximately 2 centimeters is first wrapped around the hallux 25 beginning within the inter-digital space 26 then wrapped around the foot to cover the operated zone 24.

Experimental use of the two dressing and stabilizing methods above-described demonstrated that the foam core in such a dressing can provide enough rigidity to stabilize the finger and the toe in the absence of any rigid splint elements.

While the preferred embodiments of the invention have been described, modifications can be made and other embodiments may be devised without departing from the spirit of the invention and the scope of the appended claims.

What is claimed is:

1. A surgical dressing for protecting a wound and immobilizing a body joint during healing which comprises a pad including:

a top sheet of surgical gauze;

a bottom sheet of surgical gauze;

an intermediary slab of open-cell synthetic foam material said slab having substantially flat and parallel top and bottom surfaces in contact with said top and bottom sheets respectively;

means for holding said sheets and slab in a layered configuration;

said pad having a rigidity sufficient for immobilizing said body joint when said pad is wrapped around said joint;

wherein said sheets and slab are substantially commensurate;

wherein said slab comprises a length of said foam material having a given, substantially uniform width; and which further comprises a strip of surgical gauze having a width substantially double said given width, said strip being transversally wrapped over said length of foam to form said top and bottom sheets.

2. The structure of claim 1, wherein said length of foam material has a thickness between 1 centimeter and 3 centimeters.

3. The structure of claim 2, wherein said length of foam material has a width between 3 centimeters and 20 centimeters.

4. The structure of claim 1, wherein said structure is splintless.

5. A surgical dressing for protecting a wound and immobilizing body joint during healing which comprises a pad including:

a top sheet of surgical gauze;

a bottom sheet of surgical gauze;

an intermediary slab of open-cell synthetic foam material, said slab having substantially flat and parallel top and bottom surfaces in contact with said top and bottom sheets respectively;

means for holding said sheets and slab in a layered configuration;

said pad having a rigidity sufficient for immobilizing said body joint when said pad is wrapped around said joint;

wherein said sheets and slab are substantially commensurate;

wherein said slab comprises a length of said foam material having a given, substantially uniform width;

wherein said length of foam material has a thickness between 1 centimeter and 3 centimeters;

wherein said length of foam material has a width between 3 centimeters and 20 centimeters; and wherein said top and bottom sheets and said slab are stitched together.

6. The structure of claim 5, wherein said structure is splintless.

7. A surgical dressing a for protecting a wound and immobilizing a body joint during healing which comprises a pad including:

a top sheet of surgical gauze;

a bottom sheet of surgical gauze;

an intermediary slab of open-cell synthetic foam material, said slab having substantially flat and parallel top and bottom surfaces in contact with said top and bottom sheets respectively;

means for holding said sheets and slab in a layered configuration;

said pad having a rigidity sufficient for immobilizing said body joint when said pad is wrapped around said joint;

wherein said sheets and slab are substantially commensurate;

wherein said slab comprises a length of said foam material having a given, substantially uniform width;

wherein said length of foam material has a thickness between 1 centimeter and 3 centimeters;

wherein said length of foam material has a width between 3 centimeters and 20 centimeters; and wherein said top and bottom sheets are joined together to form an envelope surrounding and partially compressing said slab.

8. The structure of claim 7, wherein said structure is splintless.

9. A surgical dressing for protecting a wound and immobilizing a body joint during healing which comprises a pad including:

a top sheet of surgical gauze;

a bottom sheet of surgical gauze;

an intermediary slab of open-cell synthetic foam material, said slab having substantially flat and parallel top and bottom surfaces in contact with said top and bottom sheets respectively;

means for holding said sheets and slab in a layered configuration;

said pad having a rigidity sufficient for immobilizing said body joint when said pad is wrapped around said joint;

wherein said sheets and slab are substantially commensurate;

wherein said slab comprises a length of said foam material having a given, substantially uniform width;

wherein said length of foam material has a thickness between 1 centimeter and 3 centimeters;

wherein said length of foam material has a width between 3 centimeters and 20 centimeters; and wherein said slab is bonded to said sheets by punctual implantation of parts of said sheets into said top and bottom surfaces.

10. The structure of claim 9, wherein said structure is splintless.

* * * * *